(12) United States Patent
Noar

(10) Patent No.: US 11,806,161 B2
(45) Date of Patent: Nov. 7, 2023

(54) METHOD AND SYSTEM FOR MONITORING INTERNAL BODILY DISORDERS BY DETECTING AND ANALYZING TISSUE FREQUENCIES

(71) Applicant: Mark D. Noar, Owings Mills, MD (US)

(72) Inventor: Mark D. Noar, Owings Mills, MD (US)

(73) Assignee: ENDOSURE INC., Sparks Glencoe, MD (US)

( * ) Notice: Subject to any disclaimer, the term of this patent is extended or adjusted under 35 U.S.C. 154(b) by 393 days.

(21) Appl. No.: 17/338,876

(22) Filed: Jun. 4, 2021

(65) Prior Publication Data

US 2022/0386950 A1  Dec. 8, 2022

(51) Int. Cl.
*A61B 5/00* (2006.01)
*A61B 5/256* (2021.01)

(52) U.S. Cl.
CPC .......... *A61B 5/4839* (2013.01); *A61B 5/0004* (2013.01); *A61B 5/256* (2021.01); *A61B 5/42* (2013.01); *A61B 5/4325* (2013.01); *A61B 5/4887* (2013.01); *A61B 5/7225* (2013.01)

(58) Field of Classification Search
CPC ..... A61B 5/4839; A61B 5/0004; A61B 5/256; A61B 5/42; A61B 5/4325; A61B 5/4887; A61B 5/7225; A61B 5/4836
See application file for complete search history.

(56) References Cited

U.S. PATENT DOCUMENTS

| | | | |
|---|---|---|---|
| 5,771,894 A * | 6/1998 | Richards | A61B 5/242 600/409 |
| 7,160,254 B2 | 1/2007 | Noar | |
| 9,474,482 B2 | 10/2016 | Devanaboyina | |
| 9,943,264 B2 | 4/2018 | Axelrod et al. | |
| 10,499,829 B2 | 12/2019 | Axelrod et al. | |
| 2015/0248833 A1 | 9/2015 | Arne et al. | |
| 2016/0045137 A1* | 2/2016 | Axelrod | A61B 5/392 600/382 |

(Continued)

OTHER PUBLICATIONS

Spitzer, Justin, Medical Wearables: Designing for Daily Life, 2021, obtained from worldwide web at HTTPS:experience.molex.com/medical-wearables-designing-for-daily-life/ on May 26, 2021.

(Continued)

*Primary Examiner* — Jonathan T Kuo
(74) *Attorney, Agent, or Firm* — Manelli Selter PLLC; Edward Stemberger

(57) ABSTRACT

A tissue disorder monitoring system includes at least two electrodes constructed and arranged to obtain analog electrical signals from a patient. An amplifier amplifies the analog electrical signals. Filter structure filters the amplified analog electrical signal. An A/D converter converts the amplified and filtered analog electrical signals to digitized electrical signals. A microprocessor circuit is constructed and arranged to execute an application that analyzes the digitized electrical signals to identify and to determine treatment data including a specific location and/or propagation of disordered tissue within the patient. A transmitter transmits data in a wireless manner. A power supply powers the device. A method locating disordered tissue in a patient is also disclosed.

23 Claims, 6 Drawing Sheets

(56) References Cited

U.S. PATENT DOCUMENTS

| | | |
|---|---|---|
| 2017/0113036 A1 | 4/2017 | Bottomley et al. |
| 2017/0231521 A1 | 8/2017 | Axelrod |
| 2017/0332961 A1* | 11/2017 | Noar ...................... A61B 5/296 |
| 2018/0256092 A1* | 9/2018 | Obma ................... A61B 5/4887 |
| 2018/0317800 A1 | 11/2018 | Coleman et al. |
| 2019/0290455 A1* | 9/2019 | Dearden ................ A61B 5/296 |
| 2019/0350483 A1* | 11/2019 | Noar ...................... A61B 5/389 |
| 2019/0350484 A1 | 11/2019 | Coleman et al. |

OTHER PUBLICATIONS

International Search Report & Written Opinion in PCT/US2022/31681 dated Oct. 27, 2022.

\* cited by examiner

METHOD AND SYSTEM FOR MONITORING INTERNAL BODILY DISORDERS BY DETECTING AND ANALYZING TISSUE FREQUENCIES

FIELD

The invention relates to a system and method for monitoring internal bodily disorders by detecting and analyzing tissue frequencies and thus, provide information for treatment of the bodily disorder.

BACKGROUND

Many internal bodily disorders such as, endometriosis, bowel obstruction, possible tumors, etc., require the use of endoscopy or laparoscopy techniques to locate and diagnose the bodily disorder so as to be later treated, for example, by surgery. These techniques are invasive, costly and require the patient to be treated in a hospital setting or at other medical facilities.

Accordingly, there is a need to provide a novel method and home-based system to non-invasively identify and determine a specific location and progression of an internal body disorder by monitoring specific frequencies that result from disordered tissue, to analyze frequency data and to transmit the analyzed data for use in treating the bodily disorder.

SUMMARY

An object of the invention is to fulfill the need referred to above. In accordance with the principles of a present embodiment, this objective is obtained by a method of locating disordered tissue in a patient. The method includes identifying a frequency range associated with a specific disordered tissue of a patient that is outside a frequency range of associated normal tissue. At least two electrodes are placed on, or in proximity to, a bodily surface of the patient. Frequency data and intensity of the frequency data is obtained by the at least two electrodes. A processor circuit analyzes the frequency data to determine if it is within the identified frequency range associated with the specific disordered tissue of the patient, and if so, determines treatment data including a specific location and/or propagation of the specific disordered tissue within the body of the patient based on the frequency data and the intensity of the frequency data. The treatment data is then transmitted to another device.

In accordance with another aspect of an embodiment, a disordered tissue monitoring system includes at least two electrodes constructed and arranged to obtain analog electrical signals from a patient. An amplifier is constructed and arranged to amplify the analog electrical signals. Filter structure is constructed and arranged to filter the amplified analog electrical signal. An A/D converter is constructed and arranged to convert the amplified and filtered analog electrical signals to digitized electrical signals. A microprocessor circuit is constructed and arranged to execute an application that analyzes the digitized electrical signals to identify and determine treatment data including a specific location and/or propagation of disordered tissue within the patient. A transmitter is constructed and arranged to transmit data in a wireless manner. A power supply is provided to power the device.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF THE EXEMPLARY EMBODIMENTS

Figure 1:
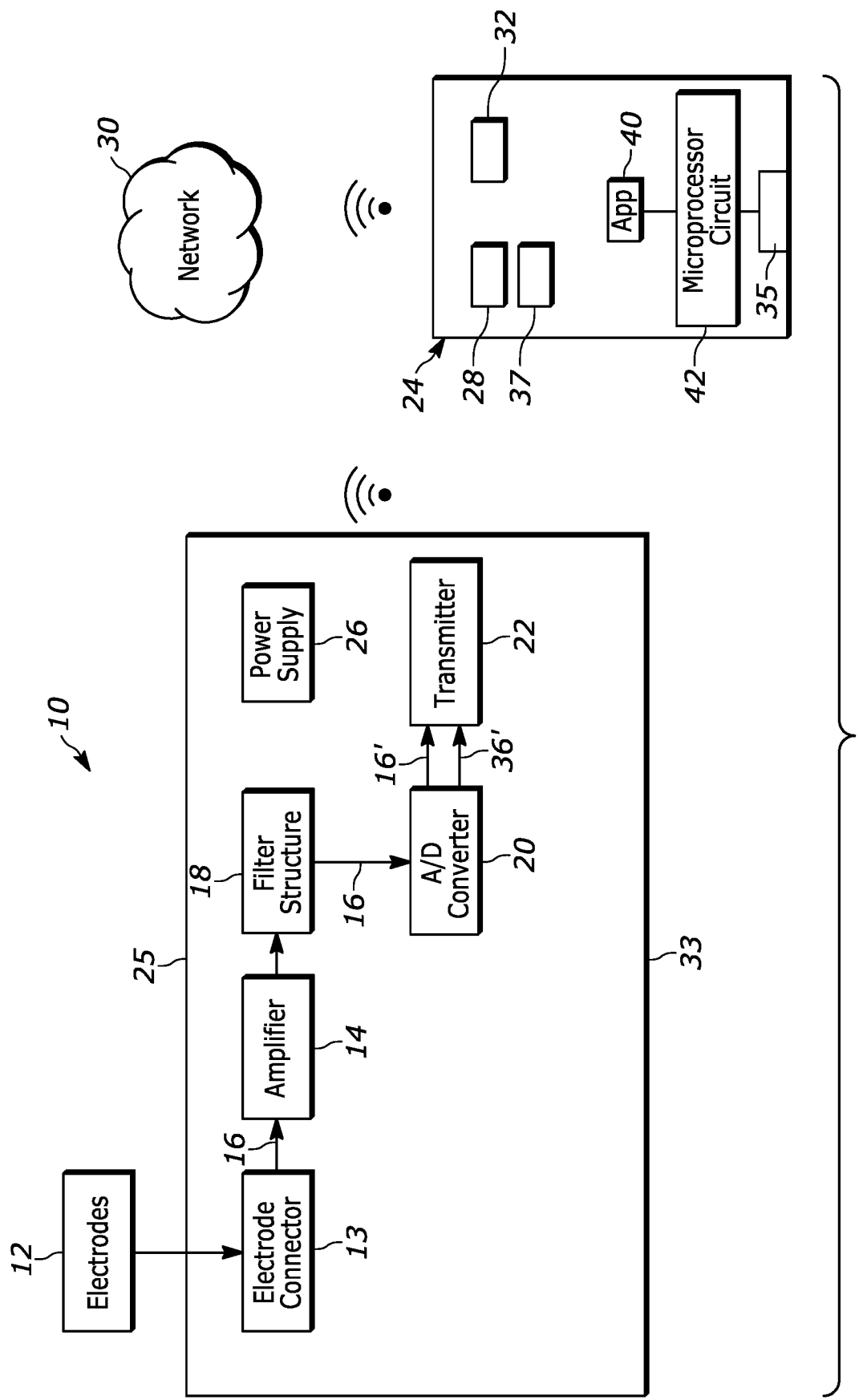
FIG. 1 is a block diagram of a disordered tissue monitoring system provided in accordance with a first embodiment of the invention.

With reference to FIG. 1, an embodiment of a disordered tissue monitoring system for monitoring and diagnosing internal bodily disorders is shown, generally indicated at 10. The system 10 includes at least two (preferably three) electrodes 12, each preferably a silver-silver chloride electrode connected, via an electrode connector 13, with an instrumentation amplifier 14 that provides the first gain stage for the electrode electrical signals 16. Filter structure 18 provides a high pass and low pass filtering of the signal 16. The filter structure 18 can include analog (hardware) or digital (software) high-pass and low-pass filters, or a combination of analog and digital filters. The amplifier 14 and filter structure 18 can be combined into a signal conditioner.

The electrical signals 16 are also passed to a 16-bit A/D converter 20. The digitized electrode electrical signals 16' including frequency signals and intensity of the frequency signals are then passed to a transmitter 22, which transfers data (e.g., signals 16') to an external portable handheld device 24 (such as a conventional smart phone, tablet, laptop) or to a network 30 in a wireless manner. When transmitted to the portable device 24, the data is received by a receiver 28 of the portable device 24. In the embodiment, the electrodes 12 are provided outside of a portable unit 25 that can be considered to be a substrate or housing. A power supply 26, such as a battery, powers the unit 25.

The portable device 24 can be considered a processing device that can also communicate in a wireless manner with the network 30 via a transmitter 32 of the portable device 24. The network 30 may include at least one of a telecommunication network such as a computer network (e.g., a LAN or a WAN), the Internet, cloud-based server, and a telephone network.

The portable device 24 can include an application (APP) 40 executed by microprocessor circuit 42 that can analyze the raw data (e.g., signals 16 including at least frequency and intensity of the frequency data) received from the transmitter 22 and provide treatment data including an identification, severity, location and progression of a bodily disorder of a patient based on the raw data. The treatment data can be stored on the network 30, shared or retrieved via the network 30, or can be stored in a memory circuit 35 of the portable device 24. Also, the portable device 24 can receive data from the network 30 via receiver 28.

The transmitter 22 can be in the form of a transceiver so as to also receive data from the portable device 24. For example, the portable device 24 may send a calibration signal 37 to the transceiver 22 that can be received by the amplifier 14 for calibration purposes and determine if the system 10 is performing within specification.

Figure 2:
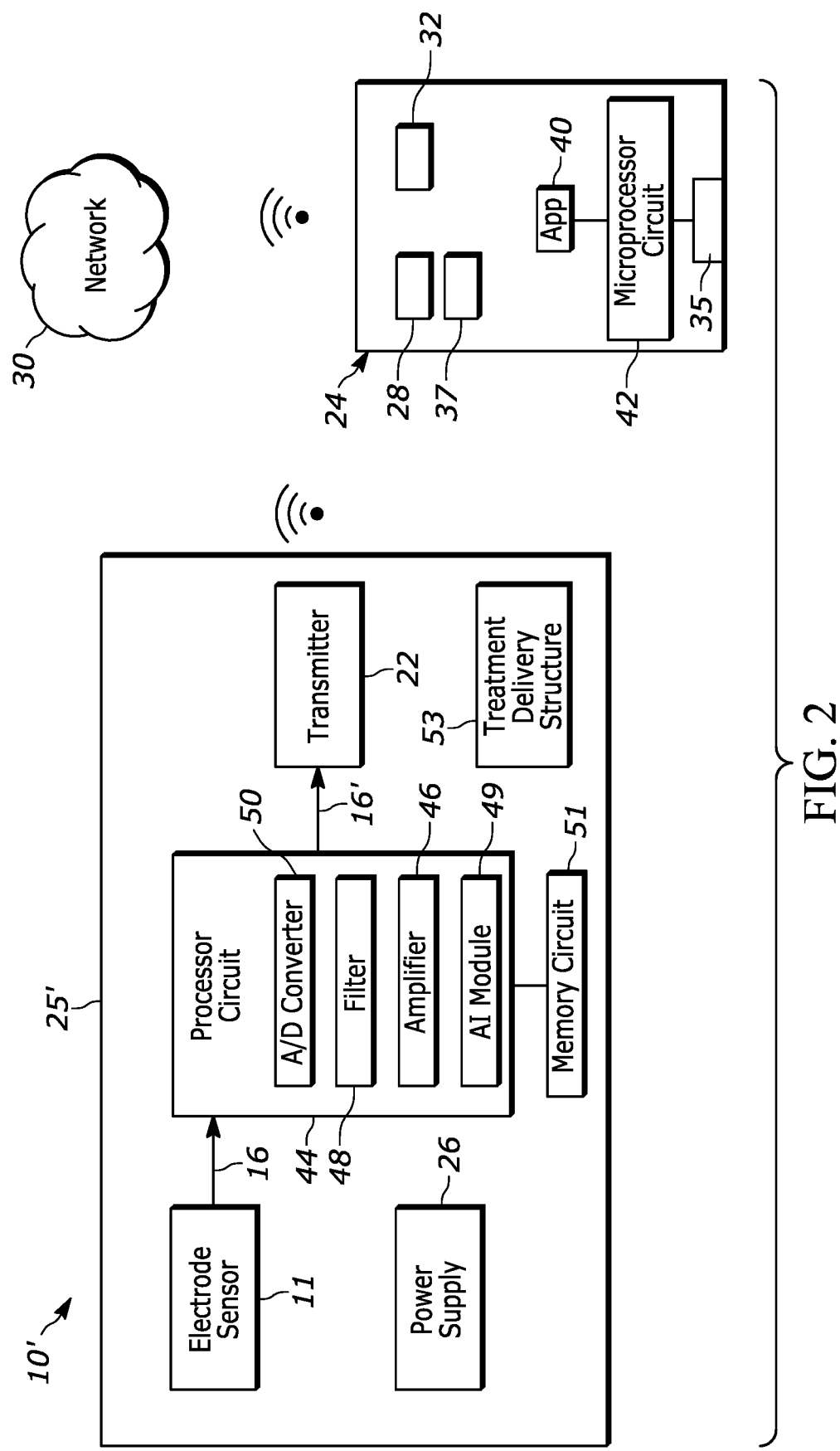
FIG. 2 is a block diagram of a disordered tissue monitoring system provided in accordance with a second embodiment of the invention.

With reference to FIG. 2, a second embodiment of the monitoring system for diagnosing internal bodily disorders is shown, generally indicated at 10'. The system 10' includes a single sensor 11 (which can include at least two or a plurality of miniaturized electrodes), disposed within the portable unit 25' and connected with microprocessor circuit 44. The microprocessor circuit 44 is provided in the unit 25' and is constructed and arranged to convert the analog electrical signal 16 to a digitized electrical signal 16' including frequency signals and intensity of the frequency signals. In the embodiment, the microprocessor circuit 44 can include an amplifier circuit 46 constructed and arranged to amplify the analog electrical signals 16, a filter circuit 48 constructed and arranged to filter the amplified analog electrical signals, and an A/D converter circuit 50 constructed and arranged to convert the amplified and filtered analog electrical signals to the digitized electrical signals 16'. The filter structure 48 preferably includes digital high-pass and low-pass filters since digital filters can be made much more accurate than their analog counterparts and are not subject to the same effects of analog component tolerances that lead to less than ideal performance from device to device and over time. Analog components can be manually sorted such that only ideal components are used, but there is considerable cost involved that will drive up the end price to the physician and these components are still subject to the ravages of environmental stresses and time that impairs their accuracy. The microprocessor circuit 44 includes an Artificial Intelligence (AI) module 49 that is configured to execute at least one algorithm to 42 that can analyze the raw data (e.g., signals 16' including at least frequency and intensity of the frequency data) and provide treatment data including an identification, severity, location and/or propagation of a bodily disorder of a patient based on the raw data. Location and propagation data can be obtained with the AI module 49 by employing conventional triangulation and/or trilateration techniques based on the frequency and intensity data obtained by at least two of the electrodes as descried further below. Alternatively, the AI module 49 can be part of APP 40 in the device 24.

A transmitter 22 is provided in the unit 25' and is constructed and arranged to transmit to the portable device 24 and/or network 30, in a wireless manner, the treatment data noted above. A power supply 26 is provided for powering the device 10'.

Gain in the preferred embodiments of the system 10, 10' is fixed and set according to the greatest peak to peak signal 16 normally expected. The 16 bit A/D converter 20, 50 provides sufficient resolution to adequately process lower level signals, such as may be recorded from a person with substantial amount of fat tissue interposed between the electrodes 12 if placed in direct contact on the skin surface, the stomach or other fatty tissue. Of course, gain may be made controllable either via an analog control or via digital control at additional cost.

Use of the wireless transmitter 22 for data communication with the portable device 24 and/or network or computer 30 removes the need for cumbersome cables and complicated interfaces that each present distinct possibilities for intermittent or total failure that can degrade system performance. The treatment data obtained can be sent wirelessly to the network 30 or portable device 24 via, for example, a cellular signal, Bluetooth® or WIFI. The memory circuit 35 or 51 each provides enough on-board memory to store an entire exam's worth of data for later transmission to the network 30.

Applicant has determined that when an internal bodily disorder is present in the body, the nerves of the tissue causing the disorder exude a specific energy (e.g., frequency) and defines a "fingerprint" of the specific tissue disorder, as compared to normal such tissue. For example, endometriosis is the condition where tissue escapes the uterus causing nervous system issues and pain. The escaped (disordered or non-normal) tissue has been identified as detectable near the proximal duodenum at a frequency range of 12-22 cpm (cycles-per-minute), and near the distal duodenum at a frequency range of 22-27 cpm.

As another example, a bowel spasm or obstruction due to scar tissue (disordered or non-normal tissue) has been identified as detectable near the distal Ileum at a frequency range of 180-200 cpm and near the small bowel at a frequency range of 50-70 cpm. In a further example, urethral disorders can be detected. A normal frequency of urethral tissue to pass urine is 7 cpm. Applicant has been determined that frequencies of at least 18 cpm and above indicates disordered or non-normal urethral tissue.

Thus, the filter structure 18, 48 of the systems 10 and 10', respectively, can be configured to detect a frequency range that is known to define the "fingerprint" of any bodily disorder.

To detect endometriosis, the filter structure 18, 48 is selected to have high pass and low pass filters to permit detection of frequencies in the range of 12 to 27 cpm. To detect a bowel obstruction, filter structure 18, 48 is selected to have high pass and low pass filters to permit detection of frequencies in the range of 180 to 200 cpm or in the range of 50 to 70 cpm, depending on where detection is aimed. To detect urethral disorders, the filter structure 18, 48 is selected to have high pass and low pass filters to permit detection of frequencies in the range of 15 to 25 cpm. These filters are generally both of second order, but higher order digital filters can be implemented. An optional second digital filter may be implemented in the software (computer readable medium) for high pass and/or low pass functions to achieve the desired bandpass filtering of the signals 16' prior to software analysis. This approach also provides greater flexibility in the system for changing specific frequency ranges in the digital filter to focus on specific bodily disorders.

Since the system 10 can be employed to locate any internal bodily tissue disorder having an energy "fingerprint", is preferable that the electrodes 12 or sensor 11 be 1) able to sense a wide area of a bodily portion, 2) either movable relative to each other and to the patient's tissue which they are to be in contact or in proximity with or 3) fixed on a grid, with the grid being movable relative to the patient's tissue which they are to be in contact or in proximity with.

Figure 3:
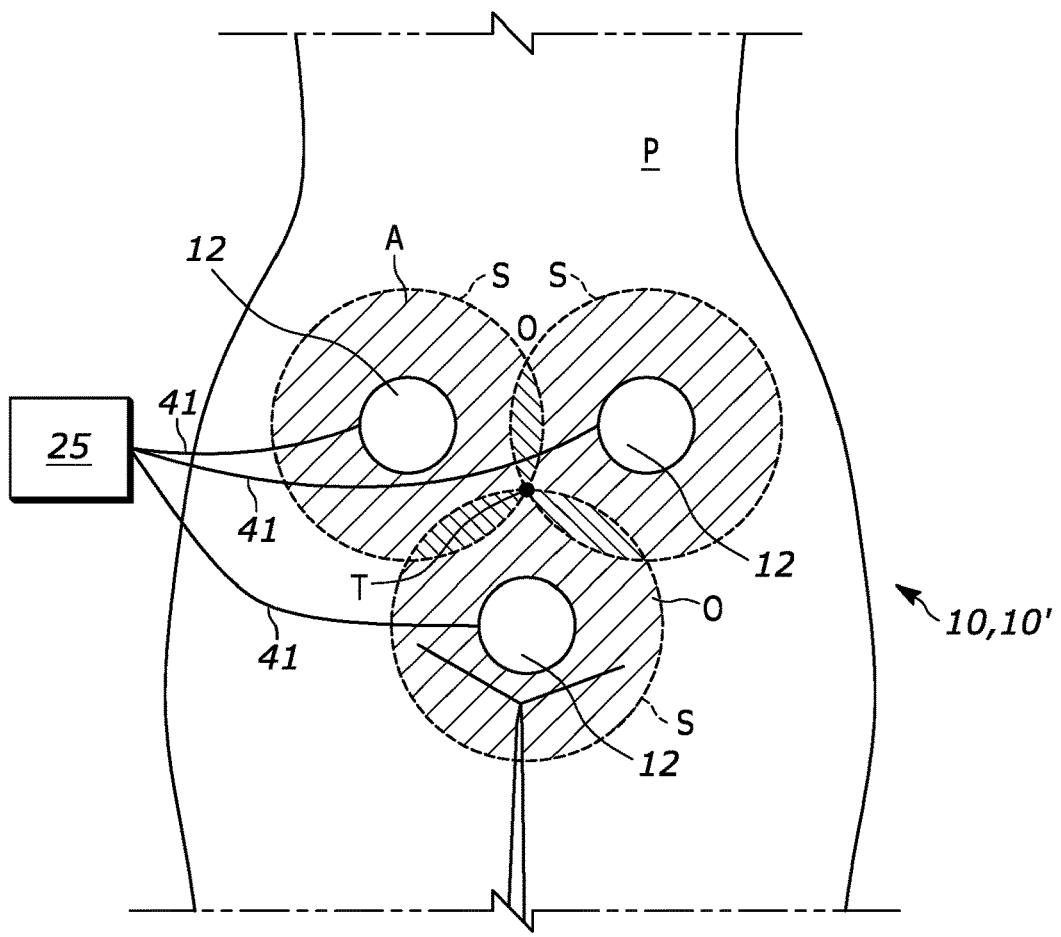
FIG. 3 is a view an embodiment of the system with electrodes thereof mounted on an abdomen of a patient.

With reference to FIG. 3, the system 10, 10' is shown employing a plurality of electrodes 12 (preferably at least three) mounted in contact with or in proximity to a body surface of a patient P. Each electrode 12 has a sensing area S to define an overall sensing area (cross-hatched at A). Sensing areas S overlap at double cross-hatched area O so that the AI module 49 of the microprocessor circuit 42 or 44 can employ triangulation and/or trilateration of the electrode signals upon obtaining the strongest frequency signal (signal intensity) to determine, severity, location and/or propagation (movement or change) of the disordered tissue in three dimensions from at least two, but preferably at least three electrodes 12. If the electrodes 12 are external to the unit 25, electrical connection 41 of each electrode 12 can be connected with the electrode connector 13 (FIG. 1) of the unit 25. The electrodes 12 are preferably disposable. Although multiple overlapping fields of detection are disclosed, it can be appreciated that instead of the plurality of electrodes, a single sensor or electrode with a wide sensing field can be provided and placed on or in proximity to the body surface. Still further, such a single, wide sensing field sensor or electrode can be implanted under the skin.

Figure 4:
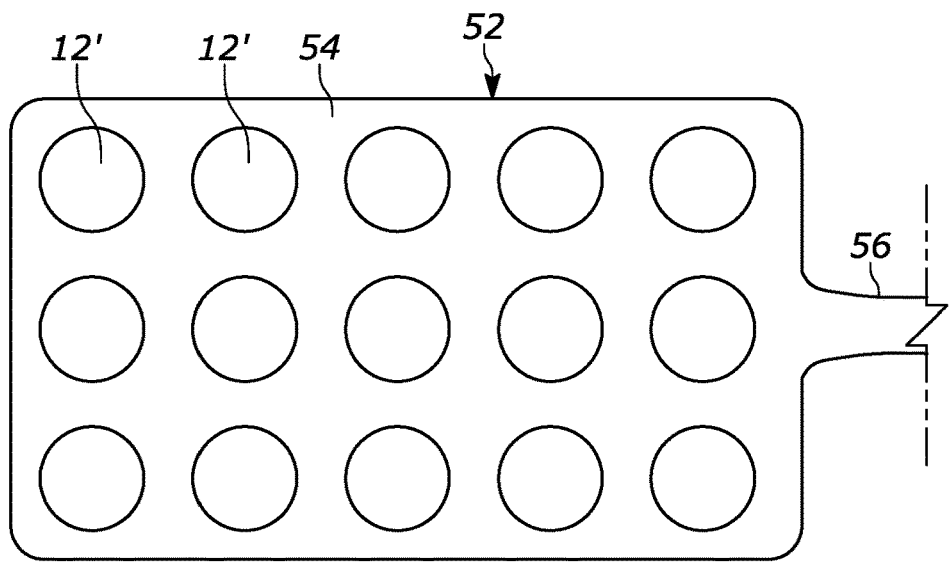
FIG. 4 is a plan view of an electrode grid for use in the system of FIG. 1.

In another embodiment and with reference to FIG. 4, an electrode array structure, generally indicated at 52, includes a plurality of electrodes 12' (preferably at least three electrodes 12'), provided in an array or grid that are fixed on a flexible substrate 54. A single connector 56 can connect with the electrode connector 13 (FIG. 1) of the unit 25. The electrode array structure 52 can be placed on the body of the patient and can be moved to different positions so that AI module 49 of the microprocessor circuit 42 or 44 can employ triangulation and/or trilateration of the electrode signals upon obtaining the strongest frequency signal (signal intensity) to determine, severity, location and propagation (movement or change) of the disordered tissue in three dimensions from at least two, but preferably at least three electrodes 12'. Alternatively, the electrode array structure 52 can be placed in a vest that is placed on the patient so that the electrodes 12' are in close proximity to the patient's skin, with the vest being movable so that the AI module 49 of the microprocessor circuit 42 or 44 can employ triangulation and/or trilateration of the electrode signals upon obtaining the strongest frequency signal (signal intensity) to determine, severity, location and propagation (movement) of the disordered tissue in three dimensions from at least two, but preferably at least three electrodes 12'. The electrode array structure 52 is preferably disposable.

Figure 5:
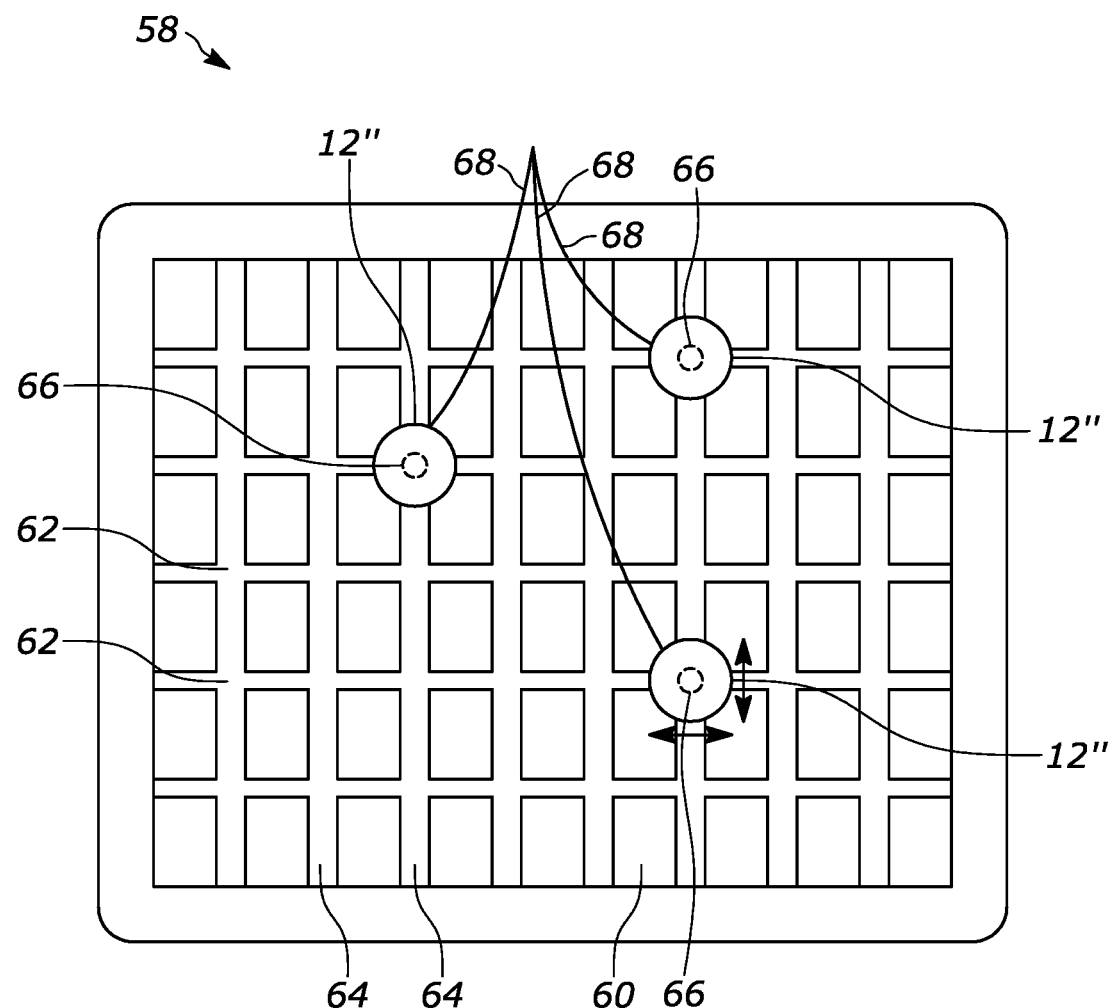
FIG. 5 is a plan view of an electrode slide structure with electrodes movable in slots thereof, for use in the system of FIG. 1.

Alternatively, instead of fixing the electrodes on a flexible substrate, with reference to FIG. 5, an electrode slide structure is shown, generally indicated at 58, that includes a flexible substrate 60 having a plurality of spaced horizontal slots 62 and a plurality of spaced vertical slots 64 therein. A plurality of electrodes 12" (preferably at least three electrodes 12") are provided, each having a base 66 that is frictionally engaged relative to the slots 62, 64 so as to be movable both horizontally and vertically with respect to the substrate 60. Electrical connections 68 of the electrodes 12" can be connected with the electrode connector 13 (FIG. 1) of the unit 25. Thus, the electrode slide structure 58 can be placed on the body of the patient and can be moved to different positions on the body and the electrodes 12" can be slid or be moved to different positions on the substrate 60 in order for the AI module 49 of the microprocessor circuit 42 or 44 to employ triangulation and/or trilateration of the electrode signals upon obtaining the strongest frequency signal (signal intensity) to determine, severity, location and propagation (movement or change) of the disordered tissue in three dimensions from at least two, but preferably at least three electrodes 12'. For example, with reference to FIG. 3, when the disordered tissue is partially in more than one of the electrode sensing areas S, using trilateration, the location T of the disordered tissue is at the intersection point of the perimeters of the three electrode areas S. If the three perimeters (circles) do not intersect at a point, then a location area would be obtained. Triangulation can be used when the disordered tissue falls within the sensing area S of only one of the electrodes.

Alternatively, the electrode slide structure 58 can be placed in a vest that is placed on the patient so that the electrodes 12" are in close proximity to the patient's skin, with the vest being movable to different positions on the body and the electrodes 12" can be slid or be moved to different positions on the substrate 60 so that the AI module 49 of the microprocessor circuit 42 or 44 can employ triangulation and/or trilateration of the electrode signals upon obtaining the strongest frequency signal (signal intensity) to determine, severity, location and propagation (movement or change) of the disordered tissue in three dimensions from at least two, but preferably at least three electrodes 12'. The electrode slide structure 58 is preferably disposable.

The electrodes 12, 12, 12" or electrode sensor 11 can detect the frequency, frequency intensity and a direction of origin of the frequency signal of disordered tissue and by using triangulation and/or trilateration as described above, treatment data including severity, location and propagation of the disordered tissue can be identified. Thus, if the frequency of the monitored tissue is within the "fingerprint" range of the specific disordered tissue, the treatment data regarding the disordered tissue is obtained. Also, a location of the disordered tissue and other characteristics such as propagation can be determined by the system 10, 10' so that treatment can be effected without further invasive endoscopy or laparoscopy locating procedures. For example, a bowel obstruction can be detected based on a certain disordered frequency of the bowel tissue as compared to a normal frequency as noted above. If the intensity (strength) of the frequency signal (e.g., caused by contacting of muscle) remains constant over a defined area, this would indicate a static location of blockage. If, however, the intensity of the frequency signal is detected to increase over a distance and then reduce, propagation (change and severity or extent) of the blockage (disordered tissue) is determined. For example, endometriosis tissue (disordered tissue) may change during a woman's menstrual cycle, as may the associated enteric nervous system spasm, or a bowel blockage can change location or involve variable portions of the gastrointestinal system. When the bowel obstruction is fixed or static, the propagation is zero. The amount of time it takes for a frequency signal to move from one location to a second location along the disordered tissue and the distance between the two locations can be obtained by the AI module 49 and used to determine the propagation of the disordered tissue and/or location of the obstruction or disorder. Thus, the system 10, 10" can determine the focal point of the disordered tissue as well as the extent of the disordered tissue, e.g., upstream, downstream or at a location different from the focal point.

Figure 7:
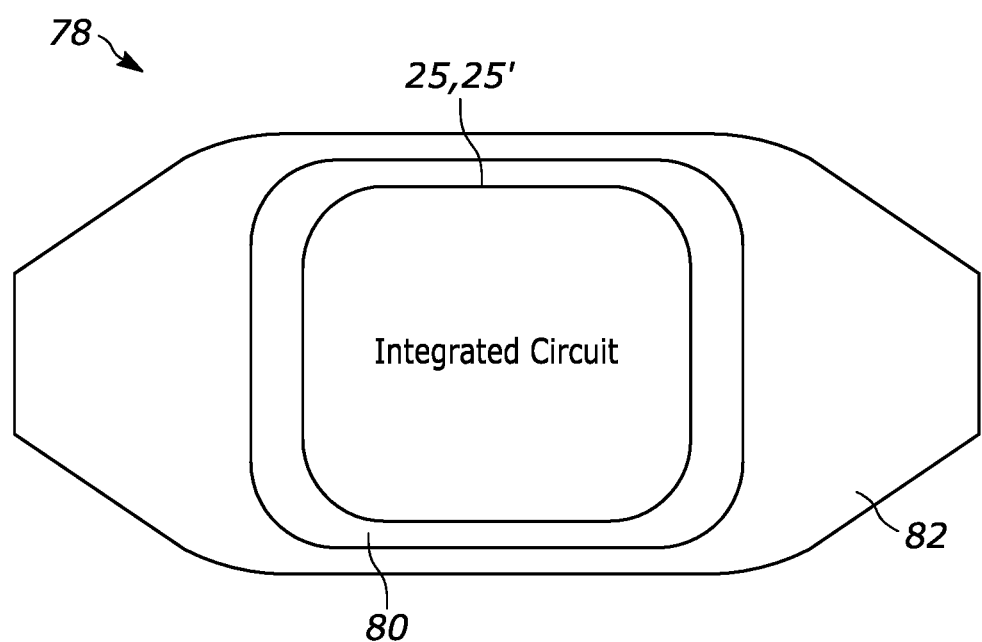
FIG. 7 is a plan view of a medical skin patch incorporating an integrated circuit containing components of the system.

It is noted that the units, 25, 25' (e.g., the at least two electrodes, the amplifier, the filter structure, the A/D converter, the microprocessor circuit, and the transmitter) can be miniaturized down to a single integrated circuit with a miniature power source as to portable, flexible wearable and disposable. Thus, the housing may not be required, or a flexible substrate of the integrated circuit can be considered to be the housing. To enhance wearability, miniaturized or not, the units 25, 25' are preferably flexible and sweat or water resistant. For example, with reference FIG. 7, if a general mounting location on the body is known, the integrated circuit 25, 25' could be configured into a medical skin patch 78 or can replace the pad of an adhesive bandage so as to be adhered and worn on the user's skin. The skin patch 78 can have a portion 80 covering over the integrated circuit and can include a mounting portion 82, the underside of which and be adhered to skin. Alternatively, the integrated circuit could be mounted on the body using a self-adhering bandage (e.g., wrapped around the abdomen), or can be incorporated on a belt, so as to be able to be moved to different locations on the body and remounted if needed. Thus, the unit 25, 25', when worn by the patient, can obtain data over a period of time.

Once the treatment data is obtained by the system 10, 10', the system 10, 10' can notify the user to initiate treatment. Treatment can be performed, for example, by modulating the disordered tissue with energy such as electro-magnetic frequency (EMF) or electric shock treatment from a treatment delivery structure 53 included in the unit 25' (FIG. 2). The treatment delivery structure 53 can be of the type disclosed in U.S. Patent Application Publication No. 20170332961 A1, the content of which is hereby incorporated by reference herein. The treatment delivery structure 53 can be separate from and outside of the unit 25' (e.g., drugs or hormones) and implanted or disposed on the body of the patient and can communicated wirelessly with the network 30 or portable device 24. The microprocessor circuit 42 or 44 can signal the treatment delivery structure 53 to deliver the treatment. Alternatively, treatment can be removal of the disordered tissue by surgery. If drug or hormone treatment is employed, the treatment delivery structure 53 that is disposed on or implanted in the patient can, instead of delivering EMF or electric shock, deliver the drug or hormone to the disordered tissue on demand as needed to calm the disordered tissue by being controlled by an APP on the portable device 24, preferably upon authorization from a doctor. For example, if the system 10, 10' detected an abnormality in the motility of the gastrointestinal tract, the treatment delivery structure 53 could deliver treatment (drug, EMF, etc.) to speed-up the motility, slow down or even stop the motility. Alternatively, if the unit 25' is in the form of an integrated circuit on a medical skin patch 78, the treatment delivery structure 53 can be the patch itself, so that the drugs or hormones can be delivered trans-dermally via the patch. The unit 25' can also have input buttons for initiating controls.

The treatment data obtained or received by the portable device 24 or computer 30 can include color-coded data. For example, different frequencies can be assigned different colors such as, the frequency indicative of abnormal tissue can be color-coded as red, while other normal frequencies can be blue in color. The intensity of the frequency signals can also be displayed with the data.

Figure 6:
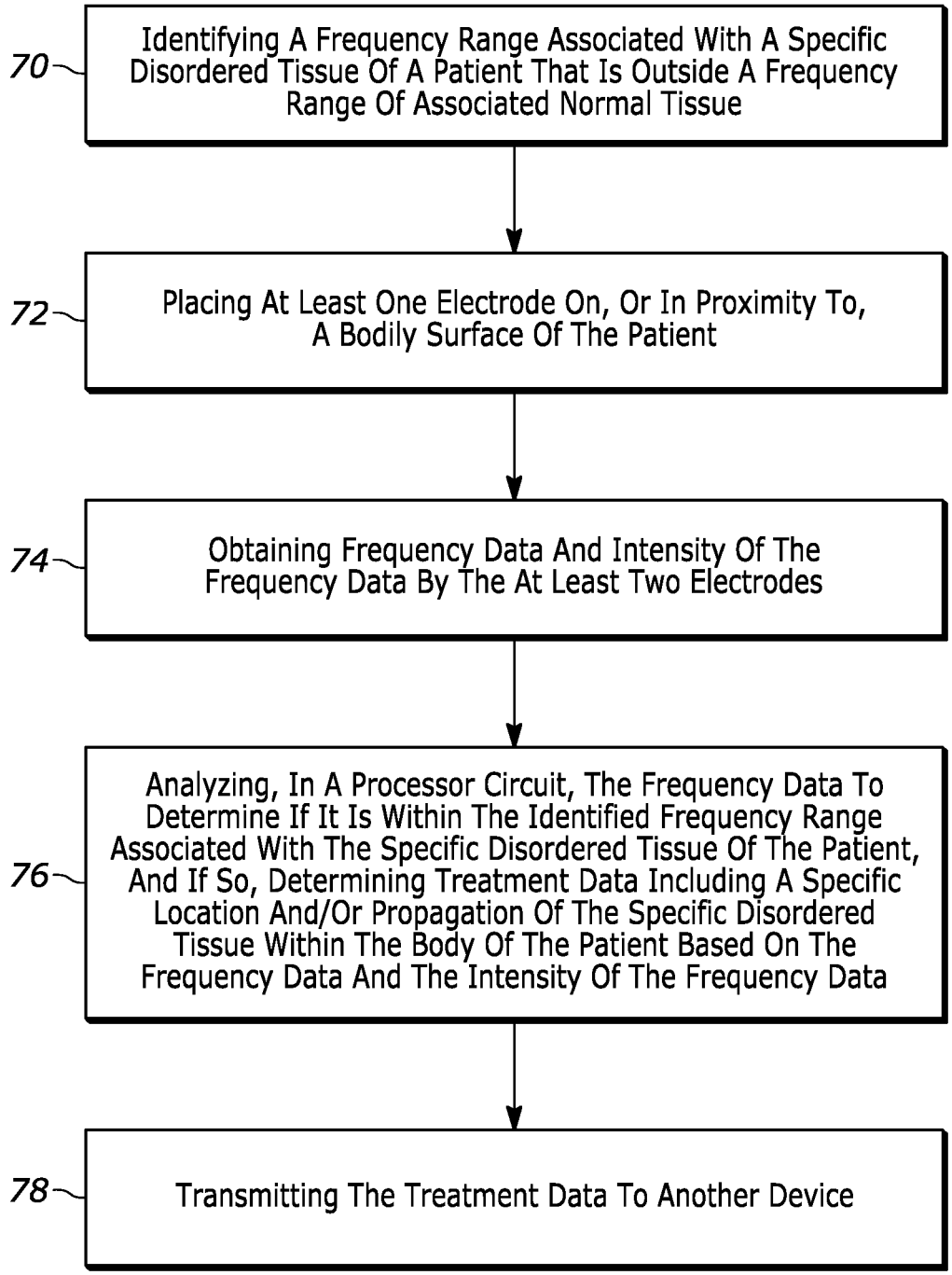
FIG. 6 is a flow chart of steps of a method of an embodiment.

Thus, by employing the algorithms outlined above, with reference to FIG. 6, a method of monitoring disordered tissue in a patient includes in step 70, identifying a frequency range associated with a specific disordered tissue of a patient (e.g., based on the "fingerprint" noted above) that is outside a frequency range of associated normal tissue. In step 72, at least one electrode 11, 12, 12', 12" is placed on, or in proximity to a bodily surface of the patient. In step 74, frequency data is obtained by the at least one electrode. In step 76, the frequency data is analyzed by the microprocessor 42, 44 to determine if it is within the identified frequency range associated with the specific disordered tissue of the patient, and if so, the AI module 49 of the microprocessor 42, 44 determines, by trilateration, a specific location of the disordered tissue within the body of the patient. In step 76, the frequency data and location data are transmitted to another device. Although, as described above, the transmission of data is preferably in a wireless manner, it is within the contemplation of the embodiment that transmission can include transferring data in a wired manner. Once a patient is known to have the disordered tissue, treatment can then be performed by, for example, modulating the disordered tissue with EMF, performing surgery, or delivering drugs or hormones to the patient. After the therapeutic treatment, the system 10, 10' can be employed again immediately thereafter, after a delayed period, or after a long period of time to determine if there is a change of the sensed frequency at the location(s) where the disordered tissue was previously identified.

Although embodiments for endometriosis and bowel obstructions have been disclosed, the system 10, 10' can be configured to located any internal bodily disorders by ensuring detecting of the proper frequency range, so long as the disorder exudes an energy "fingerprint" as noted above. For example, but not limited to, abnormal contracting or spasms of the intestines due to, for example a blockage; abnormal contracting or spasms of the stomach due to, for example an ulcer; abnormal contracting or spasms of the bladder due to, for example kidney stones could be detected by the system 10, 10'. Also, abnormal frequencies given off by tumors can be detected by the system 10, 10'.

The operations and algorithms described herein can be implemented as executable code within the microprocessor circuits 42, 44 as described, or stored on a standalone computer or machine readable non-transitory tangible storage medium that are completed based on execution of the code by a processor circuit implemented using one or more integrated circuits. Example implementations of the disclosed circuits include hardware logic that is implemented in a logic array such as a programmable logic array (PLA), a field programmable gate array (FPGA), or by mask programming of integrated circuits such as an application-specific integrated circuit (ASIC). Any of these circuits also can be implemented using a software-based executable resource that is executed by a corresponding internal processor circuit such as a micro-processor circuit and implemented using one or more integrated circuits, where execution of executable code stored in an internal memory circuit causes the integrated circuit(s) implementing the processor circuit to store application state variables in processor memory, creating an executable application resource (e.g., an application instance) that performs the operations of the circuit as described herein. Hence, use of the term "circuit" in this specification refers to both a hardware-based circuit implemented using one or more integrated circuits and that includes logic for performing the described operations, or a software-based circuit that includes a processor circuit (implemented using one or more integrated circuits), the processor circuit including a reserved portion of processor memory for storage of application state data and application variables that are modified by execution of the executable code by a processor circuit. The memory circuits 35, 51 can be implemented, for example, using a non-volatile memory such as a programmable read only memory (PROM) or an EPROM, and/or a volatile memory such as a DRAM, etc.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A tissue disorder monitoring system comprising:
at least two electrodes constructed and arranged to obtain analog electrical signals of internal bodily tissue of a patient;
an amplifier constructed and arranged to amplify the analog electrical signals;
filter structure constructed and arranged to filter the amplified analog electrical signals;
an A/D converter constructed and arranged to convert the amplified and filtered analog electrical signals to digitized electrical signals;
a microprocessor circuit constructed and arranged to execute an application that analyzes the digitized electrical signals to identify and determine treatment data including a specific location and/or propagation of disordered tissue within the patient,
a transmitter constructed and arranged to transmit data in a wireless manner; and
a power supply for powering the system,
wherein at least three electrodes are provided, each electrode having a sensing area, wherein, when the electrodes are placed on or in proximity to the patient, the sensing areas overlap,
wherein the at least three electrodes are defined in an electrode slide structure comprising a flexible substrate having a plurality of spaced horizontal slots and a plurality of spaced vertical slots therein, wherein each electrode is constructed and arranged to be movable in the horizontal and vertical slots.

2. The system of claim 1, further comprising a housing, wherein at least the amplifier, filter structure, A/D converter, power supply and transmitter are disposed in or on a housing.

3. The system of claim 2, wherein the electrodes are provided in a single electrode sensor disposed in or on the housing.

4. The system of claim 2, wherein the microprocessor circuit is disposed within or on the housing and the transmitter is constructed and arranged to transmit the treatment data.

5. The system of claim 4, wherein the amplifier, filter structure and A/D converter are part of the microprocessor circuit.

6. The system of claim 2, further comprising a treatment delivery structure constructed and arranged to deliver treatment to the disordered tissue, wherein the treatment delivery structure is provided in or on the housing and is constructed and arranged to deliver electro-magnetic frequency energy or electric shock energy to the specific disordered tissue.

7. The system of claim 4, wherein the microprocessor circuit further comprises an artificial intelligence module constructed and arranged to determine the specific location and/or propagation of the specific disordered tissue by triangulation and/or trilateration.

8. The system of claim 1, wherein the digitized electrical signals include frequency signals and intensity of the frequency signals.

9. The system of claim 1, wherein the electrodes are each constructed and arranged to sense frequency over a wide sensing field.

10. The system of claim 1, wherein the microprocessor circuit is disposed in a separate, portable device having a receiver so that data transmitted by the transmitter can be received by the receiver, with the microprocessor circuit executing the application to determine the treatment data including the specific location and propagation of the specific disordered tissue.

11. The system of claim 1, further comprising a treatment delivery structure constructed and arranged to deliver treatment to the disordered tissue.

12. The system of claim 11, wherein the treatment delivery structure is constructed and arranged to deliver electromagnetic frequency energy or electric shock energy to the specific disordered tissue.

13. The system of claim 11, wherein the treatment delivery structure is constructed and arranged to deliver energy, drugs or hormones on demand to the specific disordered tissue.

14. The system of claim 1, wherein the at least two electrodes, the amplifier, the filter structure, the A/D converter, the microprocessor circuit, the power supply and the transmitter are part of a single integrated circuit.

15. The system of claim 14, wherein the integrated circuit is constructed is flexible and is constructed and arranged to be wearable.

16. A method of monitoring disordered tissue in a patient comprising the steps of:
a) identifying a frequency range associated with a specific disordered tissue of a patient that is outside a frequency range of associated normal tissue,
b) placing at least two electrodes on, or in proximity to, a bodily surface of the patient,
c) obtaining frequency data and intensity of the frequency data of internal bodily tissue of the patient using the at least two electrodes, and
d) analyzing, in a processor circuit, the frequency data to determine if it is within the identified frequency range associated with the specific disordered tissue of the patient, and if so, determining treatment data including a specific location and/or propagation of the specific disordered tissue within the body of the patient based on the frequency data and the intensity of the frequency data, wherein the specific disordered tissue is endometriosis causing tissue, and the step of identifying the frequency range identifies the range as one of 12-22 cycles-per-minute (cpm) or 22-27 cpm.

17. The method of claim 16, further comprising, based on the treatment data, treating the specific disordered tissue with EMF, electric shock treatment, drugs, or hormones.

18. The method of claim 17, wherein the step of treating the specific disordered tissue includes on demand treatment.

19. The method of claim 18, further comprising, after the treating step, repeating c) and determining if there is a change in the frequency data.

20. The method of claim 16, wherein the analyzing step includes determining the specific location and/or propagation of the specific disordered tissue by triangulation and/or trilateration.

21. The method of claim 16, further comprising:
e) transmitting the treatment data to another device.

22. A tissue disorder monitoring system comprising:
electrodes constructed and arranged to obtain analog electrical signals from internal tissue of a patient;
an amplifier constructed and arranged to amplify the analog electrical signals;
filter structure constructed and arranged to filter the amplified analog electrical signals to pass certain frequencies of the internal tissue including a range of frequencies associated with endometrial tissue;

an A/D converter constructed and arranged to convert the amplified and filtered analog electrical signals to digitized electrical signals that include frequency signals; and a microprocessor circuit constructed and arranged to execute an application that analyzes the frequency signals of the digitized electrical signals to determine if the frequency signals are within the range of frequencies of 12-27 cycles-per-minute (cpm) associated with the endometrial tissue to thereby non-invasively determine if endometriosis is present in the patient.

23. The system of claim 22, wherein the digitized electrical signals include frequency signals and intensity of the frequency signals, and based on the frequency signals and intensity of the frequency signals, the microprocessor circuit is constructed and arranged to identify a specific location and/or propagation of the endometrial tissue within the patient.

\* \* \* \* \*